United States Patent [19]

Capetanopolous et al.

[11] Patent Number: 5,560,810
[45] Date of Patent: Oct. 1, 1996

[54] ELECTROCHEMICAL GAS SENSOR ASSEMBLY

[75] Inventors: Constantine D. Capetanopolous, Dobbs Ferry; Patrick J. Ianntta, Bellmore, both of N.Y.

[73] Assignee: SEM Corporation, Westbury, N.Y.

[21] Appl. No.: 404,970

[22] Filed: Mar. 16, 1995

[51] Int. Cl.[6] .................................................. G01N 27/26
[52] U.S. Cl. .......................... 204/408; 204/415; 204/431; 204/432; 205/780.5; 205/782.5; 205/793; 422/83; 422/88
[58] Field of Search ..................................... 204/415, 408, 204/426, 424, 431, 432, 153.14, 153.17; 422/88, 83

[56] References Cited

U.S. PATENT DOCUMENTS

| | | |
|---|---|---|
| 4,585,542 | 4/1986 | Wright et al. ........................... 204/415 |
| 4,633,704 | 1/1987 | Tantram et al. ......................... 204/415 |
| 5,085,759 | 2/1992 | Harker .................................... 204/408 |

*Primary Examiner*—Bruce F. Bell
*Attorney, Agent, or Firm*—Lee, Mann, Smith, McWilliams, Sweeney & Ohlson

[57] ABSTRACT

An electrochemical gas sensor assembly comprises an electrochemical gas sensor for sensing a selected gas. A filter is provided through which gas to be sensed must pass before reaching the sensor, the filter being adapted to prevent at least one non-selected gas from reaching the sensor but permitting passage of the selected gas. A temperature control system controls the temperature of the filter.

15 Claims, 3 Drawing Sheets

ELECTROCHEMICAL GAS SENSOR ASSEMBLY

The invention relates to an electrochemical gas sensor assembly comprising an electrochemical gas sensor for sensing a selected gas; and a filter through which gas to be sensed must pass before reaching the sensor, the filter being adapted to prevent at least one non-selected gas from reaching the sensor but permitting passage of the selected gas.

Electrochemical gas sensors are very well known and are used to sense certain gases including toxic gases and non-toxic gases such as oxygen. An example of a typical electrochemical gas sensor is described in U.S. Pat. No. 4,633,704.

The use of filters with electrochemical gas sensors is particularly important when sensing toxic gases so as to remove so-called "interfering" gases. An example of such an assembly is a nitric oxide sensing assembly in which a filter formed by silver oxide is provided to remove the cross-interfering gases sulphur dioxide and nitrogen dioxide. These two gases are removed by reacting chemically with the silver oxide ($Ag_2O$) of the filter as follows:

$Ag_2O + SO_2 + \frac{1}{2}O_2 = Ag_2SO_4$ $Ag_2O + NO_2 = Ag\ NO_3 + Ag$

Nitric oxide (NO) does not react with $Ag_2O$ and passes through the filter to the sensing electrode of the sensor where it is electrochemically detected by anodic oxidation.

$NO + 2H_2O = HNO_3 + 3H^+ + 3e$

This anodic oxidation at the sensing electrode initiates the conduction of current through an electrolyte with a counter electrode, the current being detected by an external circuit to indicate the presence and/or concentration of the nitric oxide.

Although the nitric oxide does not react chemically with the filter, it does undergo a weak physical sorption on the surface of the oxide.

This physical sorption reaches an equilibrium coverage which is characterized by the temperature of the filter and the NO gas concentration. The lower the temperature, the greater the amount of sorption and the higher the NO gas concentration the greater the amount of gas sorbed.

The process of physical sorption is reversible and desorption (or degassing) occurs when either the gas concentration is reduced or the temperature increased and vice versa. The sorption process results in a temporary, transient depression of a sensor signal on application of a gas containing NO until the sorption approaches equilibrium determined by the temperature and gas concentration. On removal of the gas, the sensor's zero or baseline signal will be elevated until the sorption reestablishes equilibrium at a lower or zero gas concentration. On elevating the temperature the signal or baseline (depending on whether or not the gas is present) will be elevated temporarily until the sorption equilibrium is reestablished at the new temperature.

It can be seen therefore that transient errors are introduced to the sensor signal and/or the baseline signal as a result of temperature fluctuations and changes in gas concentration. The magnitude and persistence of these transient effects depend on the prehistory of the sensor filter module as regards temperature, gas concentration and gas exposure time. It has been found that this introduces a broad degree of variability which can amount to as much as a few 10's of ppm, for several hours in extreme cases, for example where there is a history of prolonged exposure to gas at relatively low temperatures followed by an increase in temperature of several 10's of degrees Celsius. This would represent a particularly serious error in situations of low $NO_k$ monitoring (e.g. several 10's to several 100's of ppm).

In accordance with the present invention, an electrochemical gas sensor assembly comprises an electrochemical gas sensor for sensing a selected gas; a filter through which gas to be sensed must pass before reaching the sensor, the filter being adapted to prevent at least one non-selected gas from reaching the sensor but permitting passage of the selected gas; and a temperature control system for controlling the temperature of the filter.

We have found that by controlling the temperature of the filter it is possible to reduce errors due to temperature variations and gas concentration variations. Generally, this will be achieved by controlling the ambient temperature of the region around the filter.

Typically, the temperature of the filter is maintained relatively constant and in the region of normal temperate ambient temperatures, (for example between 20° and 25° C.) to prevent significant filter degassing and to reduce the effect of previous exposure of the filter to gas.

The temperature control system can take a variety of forms depending upon the nature of the electrochemical gas sensor. Typically, however, the temperature control system includes a temperature sensor for sensing the temperature of the filter (for example by sensing the ambient temperature around the filter); and a temperature controller responsive to the sensed temperature to control the filter temperature in a predetermined manner. Typically, the controller attempts to maintain the filter temperature substantially constant.

Conveniently, the temperature controller includes a microprocessor.

In some cases, the temperature controller can comprise an electronic cooling device such as a Peltier device. This approach takes advantage of the fact that in general it is necessary to cool the filter rather than to heat it.

In other arrangements, the temperature controller includes a fluid jacket such as an air jacket positioned about the filter.

The fluid jacket may simply pass fluid at a constant temperature but conveniently the system further includes means for controlling the temperature of the fluid in the jacket.

Typically, the fluid jacket is connected to a mixing valve to which is supplied relatively hot and relatively cold fluids, the mixing valve being controllable to adjust the proportions of the incoming fluids to achieve a resultant mixed fluid with a desired temperature.

The generation of the relatively hot and relatively cold fluids may be achieved using a vortex tube to which is supplied compressed air.

BRIEF DESCRIPTION OF DRAWINGS

Some examples of electrochemical gas sensor assemblies according to the invention will now be described with reference to the accompanying drawings, in which.

Figure 1:
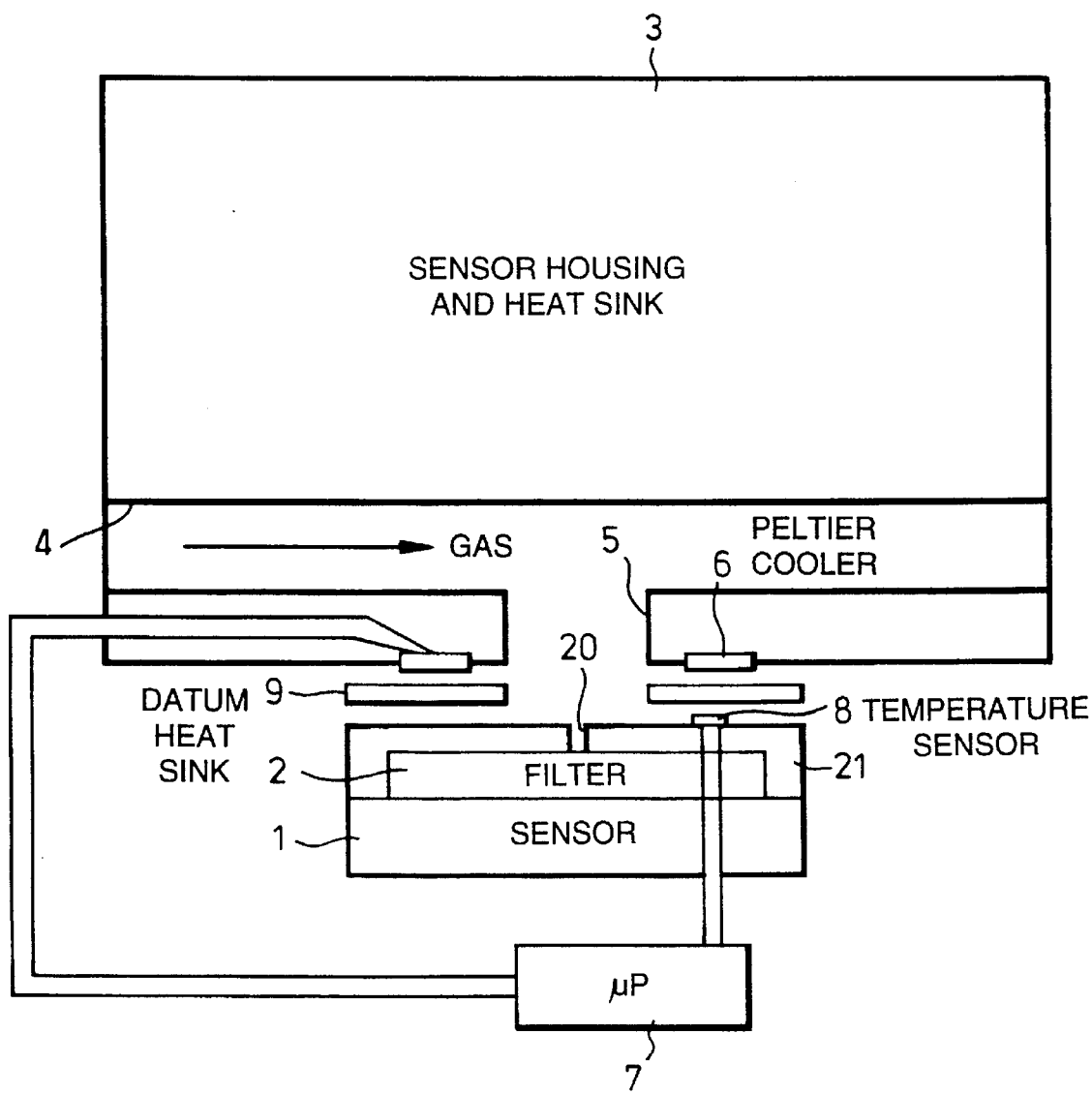
FIG. 1 is a schematic partially exploded cross-section through a first example.

The example shown in FIG. 1 includes an electrochemical gas sensor 1 which may be of the two or three electrode type on which is provided an inboard filter 2 for removing cross-interfering gases in a conventional manner. The sensor 1 and filter 2 are mounted to a sensor housing 3 which includes a gas inlet conduit 4 through which gas to be sensed is passed. The gas diffuses into a leg 5 of the conduit 4, through a capillary or capillaries 20 of either a gas phase or a Knudsen barrier 21 of conventional form, and then through the filter 2 to the sensor 1. As described above, the filter 2 is designed to prevent gases reaching the sensor 1 other than the gas to be sensed.

Typically, the filter housing will be constructed of ABS (acrylonitrile butadiene styrene) or similar plastic material or preferably of metal such as Teflon coated aluminium for more uniform temperature distribution. In a modification, it would be possible to enclose the sensor 1 also inside the aluminium heat sink 3 and thus reduce baseline effects caused by temperature rise.

The construction described so far is conventional and examples include electrochemical sensors made by SEM Corporation.

The problem with existing sensor assemblies of this type is that although the gas to be sensed (such as nitric oxide) does not chemically react with the filter 2, it nevertheless is sorbed or desorbed onto the filter 2 and the degree of sorption/desorption varies with the temperature of the filter and the concentration of the gas. As will be shown below, however, it has been found that if the filter temperature is controlled, particularly to keep it relatively cool, then not only is the variation in sorption/desorption with temperature controlled but so also is variation with gas concentration and the previous history of sensor use.

In the FIG. 1 example, control of the filter temperature is achieved via an electronic Peltier device or cooler 6 which is connected to a microprocessor 7. The microprocessor 7 is also connected to a temperature sensor 8 mounted to a datum heat sink 9 adjacent the filter 2 and the Peltier device 6.

The microprocessor 7 responds to the temperature sensed by the sensor 8 to control the temperature of the Peltier device 6 so as to maintain the filter 2 at a substantially constant temperature.

Figure 2:
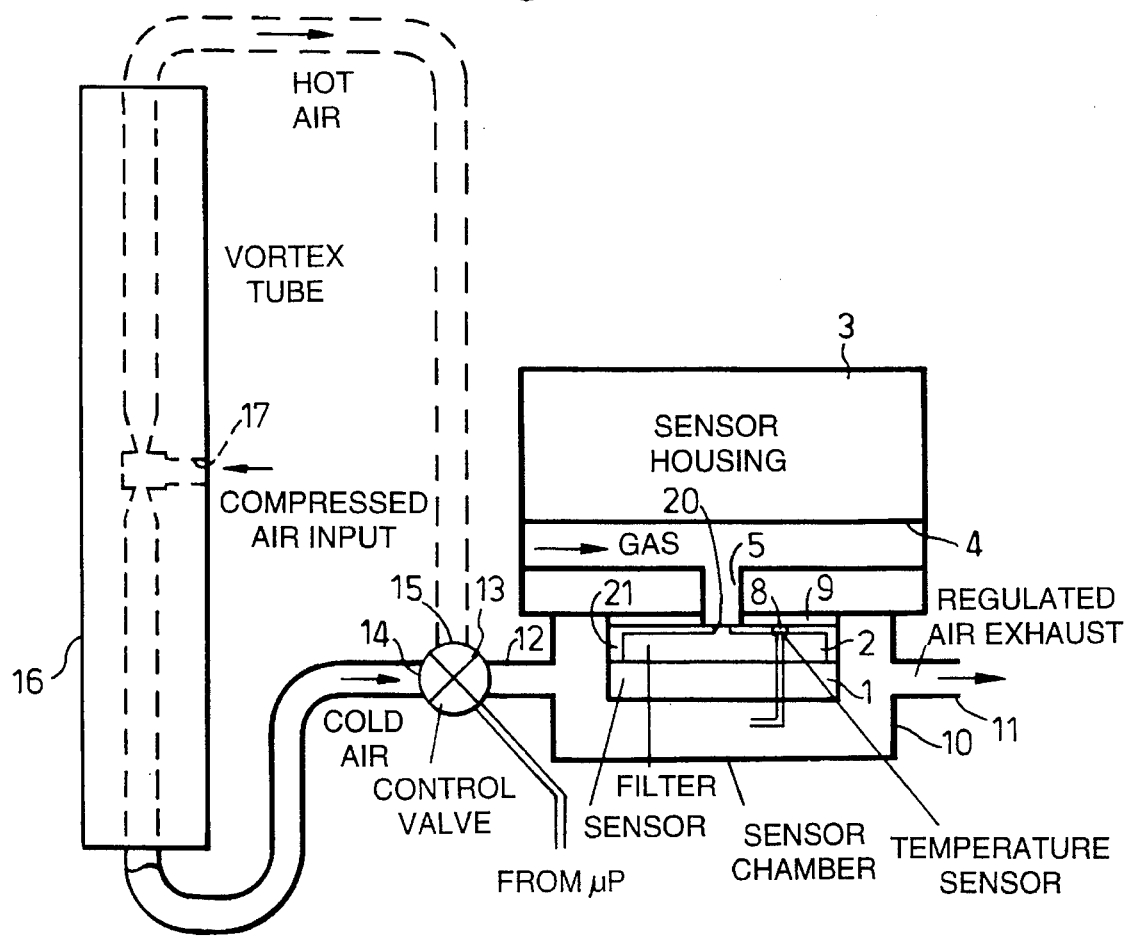
FIG. 2 is a schematic view, partly in section, of a second example.

FIG. 2 illustrates the sensor assembly shown in FIG. 1 but this time instead of using a Peltier device, an air jacket is used to control temperature. For simplicity, where elements are the same in FIGS. 1 and 2, the same reference numerals have been used and these elements will not be described further. As can be seen in FIG. 2, a jacket 10 is mounted around the sensor 1 and filter 2 and has an air exhaust port 11 and an air inlet port 12 connected to a control valve 13. The position of the control valve is controlled by a microprocessor (not shown) which is also connected to the temperature sensor 8. The control valve 13 has two inlet ports 14,15 connected to sources of cold and hot air respectively. These sources are formed by a vortex tube 16 of a conventional form to which is supplied compressed air at an inlet port 17. It will be appreciated that the control valve 13 can be adjusted in an analogue manner so as accurately to control the temperature of the air entering the jacket through the port 12 so as to control the temperature of the filter 2.

Figure 3:
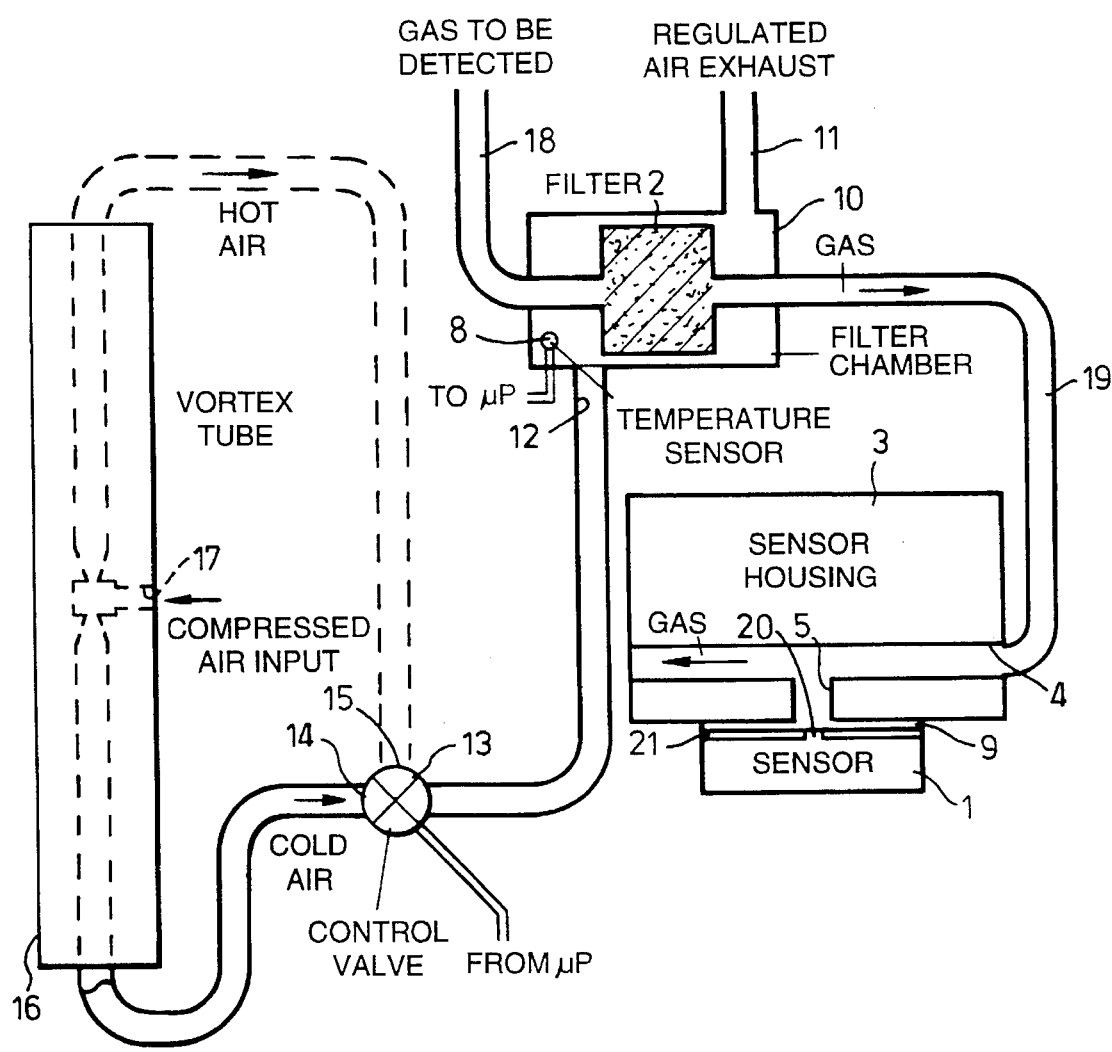
FIG. 3 is a view similar to FIG. 2 but of a third example.

In the FIGS. 1 and 2 examples, the filter 2 is mounted in board of the capillary 20. In FIG. 3, an out board filter is used whose temperature is again controlled using an air jacket in a similar way to FIG. 2. Thus, in this case, the sensor 1 is mounted directly to the heat sink 9 to receive gas through the leg 5 of the conduit 4. Up stream of the conduit 4 is the filter 2 to which gas is supplied through a conduit 18, the filtered gas being passed through a conduit 19 to the conduit 4. The temperature sensor 8 is mounted within the jacket 10 and, as in FIG. 2, is connected to a microprocessor (not shown) to which the control valve 13 is also connected. As in the FIG. 2 example, the microprocessor 13 controls the position of the control valve 13 to modify the temperature of the air entering the jacket 10 so as to control the temperature of the filter 2.

The devices shown in both FIGS. 2 and 3 are capable of both cooling and heating the filter 2 and are thus capable of maintaining the filter temperature reasonably constant. An additional advantage of maintaining the temperature of an in board filter constant (FIG. 2) results from the fact that where the sensor 1 includes a gas phase diffusion barrier defined by capillaries, these capillaries are usually located on the face of the filter. Since temperature sensitivity drifts are due chiefly to the gas temperature at the capillary input, these drifts are reduced by keeping the temperature of the filter constant.

If heating is generated by mechanisms other than ambient temperature, such as heat released by embedded electrical devices, it is possible to use a simple device such as a fan or compressed air to remove the excess heat.

In order to show the effect of controlling temperature, we have undertaken some experiments using conventional SEM electrochemical sensors fitted, where indicated, with suitable filters.

EXPERIMENT 1

Four SEM electrochemical nitric oxide sensors were tested, each fitted with a suitable cross-interference filter. The filters were conditioned (about a week earlier) by exposing them to 5000 ppm NO for two hours.

Tests were then carried out on each sensor at 23° C., while clean air (without NO) was supplied, to record the apparent baseline signal (i.e. with the filter in place) and the intrinsic baseline signal (with the filter removed). The results were:

Average apparent baseline (with filter mounted): 6–8 ppm NO.

Average intrinsic sensor baseline (filter material removed): 2–3 ppm NO.

This showed that there is a small amount of degassing at room temperature caused by exposure of the filter to 5000 ppm about a week earlier.

EXPERIMENT 2

Two SEM Corporation 3NF/F nitric oxide electrochemical sensors were tested after having been conditioned at 5000 ppm NO for two hours. In these sensors, the filters are not detachable.

Initially, the baseline signals at room temperature and at 40° C. were determined. 200 ppm nitric oxide gas was then fed to each sensor for 30 minutes and then terminated. The base line signal at 40° C. was measured.

1000 ppm nitric oxide gas was then fed to each sensor for 30 minutes and then terminated. The baseline signal was determined at 40° C.

The sensors were then returned to room temperature and the baseline signal measured and finally the baseline signal was again measured at 40° C. The results are given below:

Room temperature (23°) baseline: 5 ppm:

Baseline at 40°: 15 ppm.

After feeding 200 ppm gas for 30 min. Baseline at 40°: 24 ppm.

After feeding 1000 ppm gas for 30 min. Baseline at 40°: 26 ppm.

Return to room temperature, baseline 5 ppm.

Return to 40° C., baseline 22 ppm.

This experiment shows that filter degassing as temperature increases causes large shifts in baseline signal. Also, the degassing depends both on the temperature and history of exposure to gas. This indicates that simple electronic temperature compensation will not be accurate.

EXPERIMENT 3

A number of electrochemical nitric oxide sensors using different amounts of filter material were tested at temperatures up to 48° C. and exposures to various concentrations of gases for various time intervals.

Apparent baseline shifts as high as 60 ppm were recorded and amount of filter material, temperature exposure concentration and exposure time were factors affecting apparent baseline.

However, it was discovered that the contribution of these factors was minimal as long as the temperature was held reasonably constant in the range of approximately 20°–25° and the amount of material limited.

We claim:

1. An electrochemical gas sensor assembly comprising an electrochemical gas sensor for sending a selected gas; a filter through which gas to be sensed must pass before reaching the sensor, the filter including means for filtering out at least one non-selected gas to prevent said at least one non-selected gas from reaching the sensor but permitting passage of the selected gas; and a temperature control system for controlling the temperature of the filter.

2. An assembly according to claim 1, wherein the temperature control system comprises a temperature sensor for sensing the temperature of the filter; and a temperature controller responsive to the sensed temperature to control the filter temperature.

3. An assembly according to claim 2, wherein the temperature controller has a means to maintain the temperature of the filter within a set range.

4. An assembly according to claim 3, wherein the set range is substantially 20°–25° C.

5. An assembly according to claim 2, wherein the temperature controller has a means to maintain the temperature of the filter substantially constant.

6. An assembly according to claim 2, wherein the temperature controller includes a microprocessor.

7. An assembly according to claim 1, wherein the temperature control system comprises an electronic cooling device.

8. An assembly according to claim 7, wherein the electronic cooling device is a Peltier device.

9. An assembly according to claim 1, wherein the temperature control system comprises a fluid jacket surrounding the filter.

10. An assembly according to claim 9, wherein the fluid jacket is an air jacket.

11. An assembly according to claim 9, wherein the temperature control system includes means for controlling the temperature of the fluid in said jacket.

12. An assembly according to claim 11, wherein said temperature control means includes a mixing valve having first and second input ports to which two fluids are supplied, wherein one of the two fluids is hotter or colder than the other, so that when mixed, the combined fluids temperature is within a set range to control the temperature of the filter.

13. An assembly according to claim 12, further comprising a vortex tube for generating said two fluids, one of which is hotter or colder than the other fluid, respectively.

14. An assembly according to claim 1, further comprising a barrier adjacent said filter through which gas must pass before reaching said filter, said temperature control system also controlling the temperature of said barrier, and wherein said barrier is a gas phase diffusion barrier or a knudsen barrier.

15. An assembly according to claim 1, wherein said selected gas is nitric oxide.

* * * * *